United States Patent [19]

George et al.

[11] 3,962,413

[45] June 8, 1976

[54] PLATE METHODS FOR DIAGNOSING *BRUCELLA CANIS* INFECTION

[75] Inventors: Lisle W. George, Cortland; Leland E. Carmichael, Ithaca, both of N.Y.

[73] Assignee: Cornell Research Foundation, Inc., Ithaca, N.Y.

[22] Filed: May 14, 1974

[21] Appl. No.: 469,917

[52] U.S. Cl. ............................. 424/8; 23/230 B; 424/12; 424/92
[51] Int. Cl.² ................... C12K 1/04; G01N 31/02; G01N 33/16
[58] Field of Search .......................... 424/8, 12, 92; 23/230 B

[56] References Cited
OTHER PUBLICATIONS

Jones, J. Bacti, vol. 95, Feb. 1968, pp. 625–630.
Meyer, Am J. Vet. Res., vol. 30, Oct. 1969, pp. 1751–1756.
Alton, WHO, Monograph Ser. 55, 1967, pp. 43–52, 59–64.
Diaz, J. of Bacti, vol. 95, Feb. 1968, pp. 618–624.
The Vet. Bull., vol. 39, 1969, Abs. No. 4094.
The Vet. Bull., vol. 42, 1972, Abs. No. 4450; 6756.
Kelser, Manual of Vet. Bacti, Williams & Wilkins, Balti, 5th ed., 1948, pp. 663–668.

*Primary Examiner*—Jerome D. Goldberg
*Assistant Examiner*—A. P. Fagelson
*Attorney, Agent, or Firm*—Jones, Tullar & Cooper

[57] ABSTRACT

This invention relates to the use of *Brucella ovis* antigens to diagnose the presence of *Brucella canis* in an animal. *B. canis* is the causative agent of canine brucellosis. Further, this invention relates to a plate test where *B. ovis* antigens are employed for rapid accurate determination of *B. canis*.

18 Claims, No Drawings

PLATE METHODS FOR DIAGNOSING *BRUCELLA CANIS* INFECTION

STATE OF THE ART

A disease of dogs, canine brucellosis, caused by *Brucella canis*, is known to affect dogs. The beagle breed is one which is primarily affected by the disease.

Characteristic features of canine brucellosis in dogs are generalized lymphadentitis and splenitis, early undetected embryonic deaths or abortions, overt abortions at approximately 50 days of gestation, and prolonged vaginal discharge following abortion. Epididymitis, dermatitis of the scrotum and testicular atrophy, often unilateral, appear in infected males. Some males become sterile. Many infected dogs are free of clinical signs, though suffering from reproductive failures and loss of vigor. Persistent bacteremia is common and organisms persist in various tissues for more than a year. Infected dogs generally do not have elevated temperatures and presently, infections are only recognized by a positive agglutination test, and, if possible, by isolation of *B. canis*.

*B. canis*, canine brucellosis and the tube agglutination test for its detection are described inter alia by Carmichael, *Proc. U.S. Livestock San. A.*, 71 (1969): 517–527; Carmichael et al. *J.A.V.M.A.*, 152 (1968): 605–616; and *J.A.V.M.A.*, 156 (1970): 1726–1734; Hall, *Journal of Infectious Diseases*, 124 (1971), pgs. 615–618, and Diaz et al, *Journal of Bacteriology*, 95 (1968), pgs. 618–624, the disclosures of which are hereby incorporated by reference.

The tube agglutination test presently utilized in the routine Serodiagnosis of *B. canis* is not without drawbacks. Although this test has been demonstrated to correlate with bacteremia, technical disadvantages have limited its widespread clinical use. Production of a suitable homotypic diagnostic antigen requires considerable care because of the tendency of *B. canis* to become ropy after prolonged incubation. It has also been reported that the mucoid nature of the organism may be responsible for the lack of complete agglutination observed with some sera from infected dogs. In order to enhance the agglutination reaction, it has been recommended that the test be incubated 48 hours at 52°C., this recommendation has been criticized and a universally acceptable test procedure is not available.

Ideally a useful test would be simply performed, easily interpreted, and accurate in detecting infection.

In addition, antibody that agglutinates *B. canis* has been found in normal animals. Agglutinins which react with *B. canis* have been found, for example, in serums of dogs inoculated with *Bordetella bronchiseptics*. Experience is necessary to differentiate these reactions.

While *B. canis* is primarily a disease which infects dogs, at least a few instances of *B. canis* infections of humans have been reported.

DESCRIPTION OF THE INVENTION

It has now been found that antigen of *Brucella ovis* can be used to detect antibodies against *Brucella canis*.

It has further been found that a killed, preferably stained whole cell culture of *B. ovis*, can be utilized in a rapid accurate plate agglutination test for the detection of *B. canis* antibodies. The plate test comprises forming a film or pool by spreading a mixture of the antigen and the *B. ovis* whole cell culture and the *B. canis* suspect subject serum on a slide which is transparent or a contrasting opaque color, that is contrasting to the possible agglutination products, and observing the resultant degree of agglutination.

The plate test method of the invention is useful in detecting *B. canis* infection in any bacteremic *Brucella canis* susceptible subject, for example, animals such as the family canidae, especially dogs, or humans.

One plate test method of detecting Brucella has been described in Alton and Jones, "Laboratory Techniques in Brucellosis", World Health Organization, Geneva, Switzerland, 1967. This method comprises placing a quantity of the antigen on a transparent test plate to form a pool and adding to this antigen a quantity of the suspect subject serum and after allowing sufficient time for agglutination, observing the degree of agglutination with the use of appropriate backlighting and a contrast observation background.

Another plate test method which may be employed and preserved in the form of a card comprises the same general techniques except that the agglutination product is caused to contrast with the opaque background.

The antigen employed is preferably a killed, for example, heat killed, suspension of *B. ovis* organism; for example, a whole cell culture containing *B. ovis*, which has been killed, for example, by heating at a temperature and for a time sufficient to provide a killed whole cell culture which will agglutinate *B. canis* containing serum.

The whole cell *B. ovis* containing culture is then preferably concentrated, for example, by sedimentation, in previously weighed centrifuged tubes, the supernatant removed and the cells suspended in a saline solution, at a desired concentration. A conventional concentration is about 125 grams of cells per liter.

For use in the plate test to detect *B. canis* infection, the *B. ovis* antigen containing suspension is preferably stained. Virtually any staining material may be employed which enhances the visualization of agglutination without substantially interfering with the agglutination reaction that is having a substantial agglutination inhibiting effect or cause substantial false agglutination. The acceptability of any specific staining material may readily be determined by testing in the presence of known antigen, and positive and negative subject serum.

A typical staining solution is one wherein two parts of brilliant green and one part of crystal violet are intimately mixed, added to 300 parts of water and aged under refrigeration for six months before use. Another useful staining material is Rose bengal. This dye is especially useful where an opaque surface is employed, as the color intensity makes it especially adaptable for this use.

The amount of agglutinate staining material is an effective stain producing amount.

The total cell concentration of the cell suspension is preferable measured by means of the packed cell volume method such as described by Alton and Jones, supra. The final whole cell suspension should preferably have a concentration between about 4% and about 7%. The presently preferred concentration is about 6%.

Preferably, the pH of the whole cell suspension is controlled between about 6 and about 8. One suitable buffer which can be employed is a 0.15 molar phosphate buffer to control the pH at about 7.4. Where a staining material is employed, the choice of pH may be in part governed by the choice of dye or staining material in order to achieve maximum staining without interference with the agglutination reaction. With Rose bengal, it has been found that nonspecific agglutination is minimized by the use of greater than about 0.4 molar and preferably between about 0.6 to about 1 molar tris (hydroxymethyl)aminomethane-maleic acid buffer at a pH of between about 6.9 and 7.1 and preferably 7.0. Further, it has been found that with Rose Bengal that nonspecific agglutination is minimized by using about 0.8 grams of Rose bengal or less per 100 ml of 6% packed cell concentration *B. ovis* antigen suspension. Typically, between about .03 grams and about 0.6 grams of Rose bengal per 100 ml of 6% packed cell concentration *B. ovis* antigen suspension is employed.

As previously described, a pool or film of an admixture of the antigen preparation, e.g., the whole cell suspension, is formed by mixing the antigen and subject serum upon the plate. Preferably, the subject serum is placed upon the plate and the antigen added to the subject serum. It has been found that this technique enhances the avoidance of spurious agglutination responses. The avoidance of spurious agglutination response are further avoided by the incremental addition and mixing of the subject serum. In a typical plate test two separate tests are simultaneously conducted at varied concentrations. Pools containing 0.04 milliliter and 0.02 milliliter of subject serum are placed upon a substrate (i.e. glass plate) and 0.5 milliliter of *Brucella ovis* antigen containing whole cell suspension (6% packed cells) are added to each and the resultant agglutination observed.

It has been found that, for more reliable results, the subject serum should be obtained at least about three weeks and preferably four weeks after the onset of bacteremia, since prior to that time at least some infected subjects may demonstrate negative or at least doubtful agglutination response.

The period of time which must elapse before the degree of agglutination is measured is not unduly critical in the performance of the plate test. Generally, a five minute incubation period is allowed. Complete agglutination is generally observed to occur within two minutes. Generally, within five minutes, any agglutination products of a nature which might be formed will be observed.

The invention is further described in conjunction with the following examples, which are to be considered illustrative rather than limiting. All parts and percentages in the examples and throughout the specification are by weight unless otherwise specified.

EXAMPLE I

This example demonstrates prior art agglutination test for *B. canis* determination.

Antigen for use in the tube agglutination test was produced as described by Carmichael, "Canine Brucellosis: Isolation, Diagnosis, Transmission", Proceedings 71st Ann. Meeting, U.S. Livestock San. A., 1967 (1968), 517–527, using strain RM 6-66. Organisms used as seed for inoculum were grown aerobically at 37°C. for 48 hours on slants of Albimi Agar. Bacteria were harvested by the addition of 5.0 ml phosphate buffer saline, 0.15 M, pH 7.2 (PBS) and approximately 2.5 ml of the seed suspensions were inoculated into each of 10 Roux flasks which previously have been layered with 100 ml of Albimi Agar. The inoculum was spread over the surface of the media with sterile glass beads and the flasks were incubated aerobically at 37°C. for 48 hours.

After incubation, 10 ml of PBS was added to each Roux flask and the colonies of *B. canis* growth was removed by rolling the glass beads over the surface of the agar. The suspension thus formed was poured through 6 layers of sterile gauze and each flask was washed with an additional 10 ml of sterile PBS. The harvest from the Roux flasks was pooled and centrifuged at 10,000 G for 20 minutes. After centrifugation, the supernatant was decanted, and the precipitate pellet was washed twice with PBS. The pellet was then suspended in 50 ml of PBS and the bacteria was killed by heating at 50°C. for 1 hour. Merthiolate was then added to a concentration of 0.1% and the antigen stored at 4°C. as a stock suspension.

The tube tests were performed in the following manner. An aliquot of the concentrated stock antigen was removed and diluted with PBS to an optical density of .125 at a wave length of 420 $\mu$. The tube test was performed by the addition of 2.0 ml aliquots of diluted antigen suspension to tubes containing amounts of suspect serum equivalent to final dilutions of 1/25 through 1/2000 (0.04, 0.02, 0.01 ml, etc.). The tests were incubated at 52°C. for 48 hours before final readings were made. Agglutination reactions were scored from 0 to +4 ranging from no agglutination of antigen (zero) to complete clumping with cleaning of the supernatant (+4).

EXAMPLE II

This example demonstrates a plate test for the detection of *B. canis* utilizing *Brucella ovis* antigen. The antigen was prepared using with modification the method described by Alton et al, *Laboratory Techniques in Brucellosis*, World Health Organization, Geneva, Switzerland, 1967. *Brucella ovis* (Strain REO 1182 passage 6) was cultivated in the manner described for *B. canis* in Example I, except that an atmosphere of 10% $CO_2$ was used.

After harvesting *B. ovis* in the same manner described for *B. canis* in Example I, the organisms were suspended in PBS to a concentration of 125 grams wet cells per liter. The suspension was killed by heating for 1 hour at 52°C. and then was stained by the addition of 6 ml of staining solution per liter of suspension. The staining solution (aged for 2 months) was made from a finely ground mixture consisting of 2 grams of brilliant green and 1 gram of crystal violet. The triturated powder was dissolved in 300 ml of distilled water and the solution filtered through Whatman No. 1 filter paper and stored in the dark at 4°C.

After staining, the packed cell volume of each B. ovis preparation was determined by filling two 75 × 0.9–1.1 mm. capillary tubes, plugging them with clay and centrifuging for 5 minutes in a microhematocrit centrifuge. The suspension was diluted to packed cell volume of 6% and was filtered through a 1 cm × 1 cm column of loosely packed glass wool. Finally, merthiolate was added to a final concentration of 0.01%.

The plate test was performed on a glass plate by depositing suspect spectrum in 0.04, 0.02, 0.01 and 0.005 ml amounts. Micro-titer droppers were used to deliver one drop (0.05 ml) of the stained antigen suspension to each measured volume of serum. The drops then were spread with wooden applicator sticks over a 4 cm circular area and the plate was rocked gently for 5 minutes. The reactions were best observed by oblique illumination with fluorescent lighting. Agglutination was scored in increments from 0 to +4 as described in Example I.

EXAMPLE III

Eleven Beagle dogs raised in the Veterinary Virus Research Institute at Cornell University specific pathogen free facility were housed in isolation. The dogs were bled at the time of inoculation with B. canis. Ten ml of blood was drawn from each animal, and 5 ml was inoculated into a tube containing 5 ml Albimi brucella broth to which was added 1% sodium citrate. After incubation at 37°C. for 4 days, a loopful of the culture was removed and was streaked onto Albimi Agar plates. The plates were incubated for an additional 3 days before a final observation of growth was made. The serum harvested from the remaining 5 ml of blood was stored frozen at −20°C. until agglutination tests were performed.

Dogs then were infected by oral inoculation of approximately $10^9$ colony forming units of B. canis (OD .125 at 420 $\mu$). Blood cultures and serum samples were obtained at weekly intervals. Tube agglutination titers were determined within one week after sampling, but plate tests were not performed until all serums had been collected. At the time the serums were tested, in accordance with Example II, the samples were arranged in random order and each assigned a code number. A total of 140 samples were tested, including 15 samples obtained prior to the onset of bacteremia, 29 samples obtained 1–3 weeks after the onset of bacteremia and 96 samples obtained 3–25 weeks after the onset of bacteremia.

Tube and plate tests also were compared using 74 serum samples collected from two commercial breeding kennels and 73 samples submitted by veterinarians requesting B. canis serology.

EXAMPLE IV

The following examples demonstrate the specificity of the plate test and efficiency of the plate test.

When a killed B. ovis suspension of approximately 4% packed cell volume was added to 0.04 ml amounts of serum obtained from dogs infected with B. canis, granular agglutination of antigen as observed within 1 minute. Agglutination was not observed when the antigen was added to serums obtained from specific pathogen free dogs but, when it was added to serums in which low titers of non-specific agglutinins which reacted with B. canis were present, some agglutination at lower dilutions was observed. To determine whether increases in antigen concentration could mask these non-specific reactions, antigen standardized to concentrations equivalent to 4, 6, 8 and 10 percent packed cell volumes were used to titrate serums from 4 dogs bacteremic with B. canis and serums from 4 dogs not infected with B. canis, but which had antibodies at tube titers less than 1/100. When antigen concentrations greater than 4% were employed, agglutination was reduced or eliminated in some serums from normal dogs that reacted non-specifically in the tube test. However, antigen prepared at concentrations greater than 6% packed cells consistently gave lower titers in samples obtained from bacteremic animals. For this reason antigen containing a 6% packed cell volume is preferred for routine use.

To determine diagnostically significant titers, plate agglutination tests were performed on serial serum samples obtained from 11 infected dogs. All serums collected after dogs were bacteremic for 7 weeks, completely agglutinated plate test antigen in the 0.04 and 0.02 ml serum volumes. In addition, 34 of the 44 serums obtained from dogs bacteremic for 3 to 7 weeks completely agglutinated plate test antigen in both initial serum volumes. All of the remaining samples agglutinated 100% and 75% of the antigen in the 0.04 and 0.02 ml serum volumes respectively.

In addition to the strong reactions in the 0.04 and 0.02 ml serum volumes, samples from dogs bacteremic for more than 3 weeks always agglutinated some antigen in both the 0.01 and 0.005 ml serum volumes, but the amount was observed to vary between 25% and 100% for each of the two low serum amounts.

Table 1

Typical plate test reactions observed with sera obtained from dogs bacteremic with B. canis and with serum obtained from normal dogs but which cause agglutination of B. canis antigen.

| Tube Titer | Blood Culture | Plate Agglutination | | | |
|---|---|---|---|---|---|
| | | .04 | .03 | .02 | .01 |
| 200 | + | +4 | +4 | +3 | +1 |
| 500 | + | +4 | +4 | +4 | +4 |
| 250 | + | +4 | +4 | +4 | +3 |
| 25* | − | +2 | +2 | − | − |
| 50* | − | +2 | +1 | − | − |

*Partial agglutination was observed at this dilution.

Similarly, the plate test antigen usually was agglutinated more extensively in the 0.01 and 0.005 ml serum volume by samples having high tube titers (greater than 1:200) than by samples having low tube titers (less than 1:200), a reliable correlation between the agglutination at each tube dilution valve and each plate test serum volume, however, was not observed. That is, of the 140 samples tested, 14 had tube titers of 1:200 and failed to agglutinate more than 50% of the plate test antigen at the 0.01 ml serum volume. Conversely, 10 samples had tube titers between 1:125 and 1:100 and agglutinated more than 50% of the plate test antigen in one or both of the two terminal dilutions. Because of these inconsistencies, it was not possible to equate individual tube and plate test serum dilutions as has been done with other plate testing procedures. Any serum was considered positive, which caused complete agglutination (+4 reaction) of plate test antigen in the first 0.04 ml serum volume and 75% or greater agglutination in the 0.02 ml serum volume.

It was found that 16 out of 29 of the samples (55%) obtained from dogs with bacteremia for three weeks or less were classified positive by both methods. However, 95 out of 96 samples (99%) obtained between four and 25 weeks after onset of bacteremia were classified correctly with the plate test; 94 samples (98%) were classified correctly with the tube test. The single sample incorrectly classified by the plate test agglutinated 75% of the antigen in the 0.04, 0.02, and 0.01 ml serum amounts, while serums from infected dogs classified improperly by the tube method reacted with antigen at a titer of 1/50.

Prozones were observed with plate test antigen in four of the positive serums, but diminution of agglutination appeared to be limited to the 0.04 ml serum volume. In all four samples, the serums agglutinated 75% of the antigen at the initial 0.04 ml serum volume and 100% of the antigen in the remaining three serum volumes. Samples obtained prior to the onset of bacteremia were consistently negative by both tests.

When the tube and plate tests were compared by testing 74 serum samples from 2 kennels and 75 samples from the clinicians requesting *B. canis* serology, there was excellent correlation between results of the two tests.

Table 2

Comparison of the tube test and plate test in detecting *B. canis* agglutinins in samples obtained from veterinarians requesting *B. canis* serology.

| Source | Tube Test Classed Positive | Tube Test Classed Negative | Plate Test Classed Positive | Plate Test Classed Negative |
|---|---|---|---|---|
| Kennel A | 0 | 15 | 0 | 15 |
| Kennel B | 0 | 59 | 0 | 59 |
| Clinical Samples | 12 | 61 | 12 | 61 |
| Totals | 12 | 135 | 12 | 135 |

All 74 samples from kenneled animals were classified negative by both the plate and tube test procedures. Equally good correlation between the results of the tube and plate tests was observed when 73 clinical samples were examined. Of the serums tested, 12 had antibody at tube titers of greater than 1:100. Moreover, these serums also agglutinated plate test antigen at the defined diagnostic level. It was possible to obtain blood cultures from only five of the twelve dogs whose sera were classified positive. *B. canis* was isolated from the blood of all five animals. Several serums (four samples) exhibited low titered reactions in the tube test, causing partial agglutination at dilutions of 1:50 or 1:00. After five minutes of reaction time, the serum agglutinated as much as 75% of the plate antigen in the 0.04 serum amount but, in no case was antigen completely agglutinated in either the 0.04 or 0.02 ml serum volumes. Serums that were negative by tube test also were negative by plate test.

To determine whether these cross reactions could be caused by antigens of related gram negative organisms, several antiserums prepared against *B. abortus* and other gram negative organism were tested with *B. ovis* plate antigen and *B. canis* tube antigen.

Table 3

Comparison of plate and tube reactions using antisera against related organisms.

| Antiserum | Titer Against Homologous Strain | *B. canis* Tube Titer | Plate Agglutination .04 | .02 | .01 | .005 |
|---|---|---|---|---|---|---|
| *B. abortus* | 800 | — | — | — | — | — |
| *B. bronchiseptica* 1 | 800 | 1/100$^P$ | — | — | — | — |
| *B. bronchiseptica* 2 | 50 | — | — | — | — | — |
| *B. ovis* | 500 | 500 | 4 | 4 | 4 | 3 |
| *B. canis* | 250 | 250 | 4 | 4 | 4 | 3 |

$^P$indicates partial agglutination at this level.

Although some *B. bronchiseptica* and *B. abortus* antiserums were observed to cause partial agglutination of tube antigen, the plate antigen was not agglutinated. *B. ovis* antiserum agglutinated both plate and tube antigens at the diagnostic level. Such reactions were indistinguishable from those caused by *B. canis* antiserum.

EXAMPLE V

The following example demonstrates a plate test employing an opaque white background.

A buffer solution was prepared by admixing 200 ml of a first aqueous solution of tris(hydroxymethyl)aminomethane (242 grams/liter) and maleic acid (232 grams/liter), and 78 ml of a second 5 normal sodium hydroxide solution. This admixture was then made up to one liter with distilled water. The resultant solution is hereinafter referred to as 0.8 molar tris buffer.

A 1% dye solution of Rose bengal was prepared by dissolving one gram of Rose bengal in 100 ml of distilled water.

An antigen preparation was formed by adding 5 ml of the above dye solution to 100 ml of a killed *B. ovis* suspension and allowing the mixture to stand overnight. The suspension was then centrifuged and the precipitate washed three times with 0.8 molar tris buffer, and then resuspended at a 6% packed cell volume in 0.8 molar tris buffer. The pH of the suspension was 7.0. The suspension was filtered through glass wool.

On a white opaque sheet (white coated Masonite fiber board), there were pools of suspect blood serum (0.04, 0.02, 0.01, 0.005, respectively). There was added to each 0.05 ml of *B. ovis* antigen (prepared as hereinabove). After waiting three minutes, the results were observed and evaluated. At 0.04 and 0.02 suspect serum, an estimated agglutinate of 75%, was considered positive.

Eleven dogs, known as S.P.F. negative dogs, were bled to obtain 63 blood serum samples, all of which tested negative in the tube test as in Example I (tube), the plate test as in Example II (C.V.) and the plate test described hereinabove (R.B.). The dogs were orally infected with *B. canis* and blood cultures taken each week from which blood serum was obtained and tested for agglutination of all three methods (tube, C.V. and R.B., as above):

| 1–5 Weeks | 6–45 Weeks |
|---|---|
| 80% *B. canis* positive (R.B.) | 100% *B. canis* positive (R.B.) |
| 53% *B. canis* positive (C.V.) | 95% *B. canis* positive (C.V.) |
| 71% *B. canis* positive (tube) | 98% *B. canis* positive (tube) |

In a similar manner 77 field derived dog blood serum samples were tested by all three methods, as above:

| Tube | Plate - C.V. | Plate - R.B. |
|---|---|---|
| 65 *B. canis* negative | 67 *B. canis* negative | 65 *B. canis* negative |
| 9 *B. canis* positive | 9 *B. canis* positive | 10 *B. canis* positive |
| 3 indeterminate | 1 indeterminate | 1 indeterminate |

EXAMPLE VI 243 field derived dog blood serum samples were tested by both the tube method, as in Example I, as well as the plate test method of Example II

| Tube Method | Method of Example II |
| --- | --- |
| 21 *B. canis* positive | 20 *B. canis* positive |
| 221 *B. canis* negative | 220 *B. canis* negative |
| 1 indeterminate (less than 75% agglutination) | 1 indeterminate |

Other dye, buffer or adjuvants may be added to replace those exemplified. Likewise, the techniques described may be varied within the practice of the art while obtaining equivalent results.

According to the provision of the Patent Statutes there are described above the invention and what are now considered its best embodiments; however, within the scope of the appended claims, it is to be understood that the invention can be practiced otherwise than specifically described.

What is claimed is:

1. A plate test method of diagnosing *Brucella canis* infection in a subject susceptible to *Brucella canis* infection which comprises:

a. placing a quantity of blood serum of said subject upon a plate substrate and b. admixing therewith a killed whole cell suspension comprising *Brucella ovis* antigen containing an agglutinate staining, substantially non-agglutination interfering amount of a dye, said suspension having a pH between about 6 and about 8, c. wherein the formation of a visible agglutination product in the resulting mixture is indicative of *Brucella canis* infection.

2. The method of claim 1, where the dye comprises a dye selected from the group crystal violet and Rose bengal.

3. The method of claim 1 where the bacteremia susceptible subject is an animal of the family canidae.

4. The method of claim 1 where the bacteremia susceptible subject is a dog.

5. The method of claim 1 where the blood serum was obtained at least about three weeks after the suspected onset of *Brucella canis* bacteremia.

6. The method of claim 1 where the substrate is transparent.

7. The method of claim 6 where the dye comprises crystal violet.

8. The method of claim 1 where the substrate is opaque and of a color contrasting that of the agglutinate.

9. The method of claim 8 where the dye comprises Rose bengal.

10. The method of claim 1 where the *Brucella ovis* antigen suspension has between about 4% and about 7% cell concentration measured by the packed cell method.

11. The method of claim 10 where the suspension has about 6% cell concentration measured by the packed cell method.

12. The plate test method of diagnosing *Brucella canis* infection in a *Brucella canis* infected subject which comprises:

a. placing a quantity of blood serum of a *Brucella canis* infected subject, said subject having been infected by *Brucella canis* for at least about three weeks, upon a plate substrate, and b. admixing therewith a killed whole cell suspension comprising *Brucella ovis* antigen containing an agglutinate staining, substantially non-agglutination interfering amount of a dye, said suspension having a pH between about 6 and about 8, c. thereby forming, in the resulting mixture, a visible agglutination product indicative of *Brucella canis* infection.

13. The method of claim 12 where the substrate is transparent and the dye is a mixture of brilliant green and crystal violet.

14. The method of claim 12 where the substrate is opaque and the dye is Rose bengal.

15. The method of claim 12 where the subject has been infected by *Brucella canis* for at least about four weeks.

16. The method of claim 15 where the antigen suspension has a cell concentration of about 4% to about 7% measured by the packed cell method and wherein about ratio of antigen suspension to subject serum is between about 0.5:0.4 to 0.5:.05.

17. The method of claim 16 where the pH of the antigen suspension is between about 7.3 and about 7.5 and the dye comprises a mixture of brilliant green and crystal violet.

18. The method of claim 16 where the pH of the antigen suspension is between about 6.9 and about 7.1 and the dye comprises Rose bengal, the Rose bengal being present in an amount equivalent to between about 0.3 grams to about 0.6 grams per 100 ml of an antigen suspension having a 6% packed cell concentration.

* * * * *